United States Patent [19]

Reisner et al.

[11] 4,024,139

[45] * May 17, 1977

[54] 2,3,4,4A-TETRAHYDRO-10H-1,2-OXAZINO[3,2-B](1,3)BENZOXAZIN-10-ONES

[75] Inventors: David B. Reisner, Hightstown; Bernard J. Ludwig, North Brunswick; Harold M. Bates, East Brunswick; Frank M. Berger, Princeton, all of N.J.

[73] Assignee: Carter-Wallace, Inc., New York, N.Y.

[ * ] Notice: The portion of the term of this patent subsequent to Aug. 15, 1989, has been disclaimed.

[22] Filed: May 8, 1972

[21] Appl. No.: 250,909

Related U.S. Application Data

[63] Continuation-in-part of Ser. No. 809,930, March 24, 1969, Pat. No. 3,684,805.

[52] U.S. Cl. .......................... 260/244 R; 424/284
[51] Int. Cl.[2] ........................................ C07D 498/02
[58] Field of Search ........................... 260/244 R

[56] References Cited

UNITED STATES PATENTS 3,684,805  8/1972  Reisner et al. ................. 260/244

FOREIGN PATENTS OR APPLICATIONS 2,013,023  3/1970  Germany ......................... 260/244

*Primary Examiner*—John D. Randolph
*Attorney, Agent, or Firm*—Kevin B. Clarke

[57] ABSTRACT

Chemical compounds of the formula:

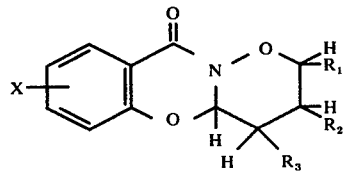

wherein X is hydrogen, hydroxy, halogen, lower alkyl, lower alkoxy, nitro, amino, acetamido, sulfonamido or trifluoromethyl, and each R is selected from the group consisting of hydrogen and lower alkyl. Said compounds have valuable anti-inflammatory activity in standard laboratory animals.

2 Claims, No Drawings

2,3,4,4A-TETRAHYDRO-10H-1,2-OXAZINO[3,2-B](1,3)BENZOXAZIN-10-ONES

This application is a continuation-in-part of application Ser. No. 809,930 filed Nov. 24, 1969 now U.S. Pat. No. 3,684,805.

The present invention relates to novel chemical compounds. More particularly, the invention relates to novel compounds which possess useful pharmacological properties.

The compounds of the present invention, which can be classified as 2,3,4,4a-tetrahydro-10H-1,2-oxazino(3,2-b) (1,3)benzoxazin-10-ones, can be represented by the following general formula:

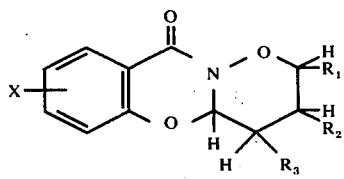

wherein X is hydrogen, hydroxy, halogen, lower alkyl, lower alkoxy, nitro, amino, acetamido, sulfonamido or trifluoromethyl, and each R is selected from the group consisting of hydrogen and lower alkyl. When X is amino, the compounds can be used in the form of their non-toxic pharmaceutically acceptable acid addition salts, such as the hydrochloride, citrate, maleate, and the like. As used herein and in the appended claims, the terms "lower alkyl" and "lower alkoxy" signify alkyl and alkoxy radicals having from one to six carbon atoms.

The compounds of the invention can be conveniently prepared according to the following synthetic route:

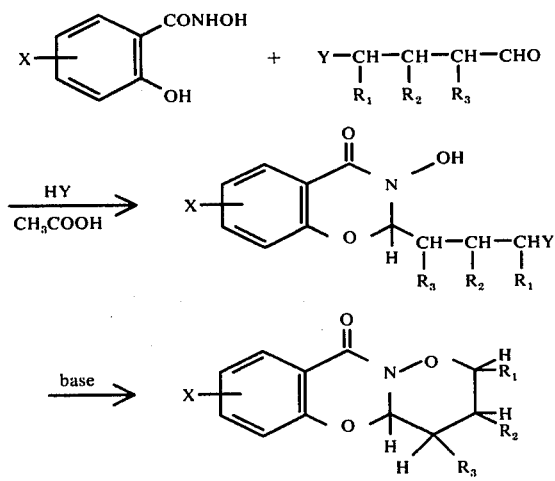

In the first reaction step, a salicylhydroxamic acid, substituted or unsubstituted, is reacted with the appropriate halo-aldehyde or its acetal, in a medium such as acetic acid, ethanol, dimethylformamide, benzene and mixtures thereof, in the presence of hydrogen halide, to yield the desired intermediate. The reaction is carried out at a temperature of from about 20° to about 70° C. The intermediates, which can be classified as 2(3-haloalkyl)-2,3-dihydro-3-hydroxy-4H-1,3-benzoxazin-4-ones, are novel compounds.

Cyclization of the intermediate under basic conditions yields the desired product. Said cyclization can be carried out using organic or inorganic bases in appropriate solvents.

The following Examples illustrate the preparation of 8-chloro-2,3,4,4a-tetrahydro-10H-1,2-oxazino(3,2-b)(1,3) benzoxazin-10-one.

EXAMPLE 1

Preparation of 8-chloro-2,3,4,4a-tetrahydro-10H-1,2-oxazino (3,2-b)(1,3)benzoxazin-10-one 6-Chloro-2-(3-chloropropyl)-2,3-dihydro-3-hydroxy-4H-1,3-benzoxazin-4-one was prepared by adding 250 ml. of glacial acetic acid saturated with hydrogen chloride gas to 37 g. of 5-chlorosalicylhydroxamic acid. 4-Chlorobutyraldehyde diethyl acetal (34 g.) and 50 ml. of glacial acetic acid saturated with hydrogen chloride gas were then added simultaneously with stirring at a rate to maintain a temperature of 25° to 40° C. The resulting mixture was stirred and heated at 55° to 60° C. for 2 hours and then allowed to stand at room temperature overnight. Mixture was poured into a mixture of ice and water, and when oil solidified it was removed by filtrating, washed with water, and air-dried. The crude product weighed 31.5 g. and melted at 70°–75° C. A sample recrystallized from ligroin at 80°–81° C.

A mixture of 10 g. of crude 6-chloro-2-(3-chloropropyl)-2,3-dihydro-3-hydroxy-4H-1,3-benzoxazin-4-one prepared in the manner hereinbefore described and 50 ml. of 15 percent aqueous solution of ammonium hydroxide was stirred for 5 hours at room temperature and then filtered and washed with water. The crude product (6 g.) was recrystallized from 45 ml. of ethanol yielding 3.8 g., m-p. 148°–149° C.

EXAMPLE 2

Preparation of 2,3,4,4a-tetrahydro-10H-1,2-oxazino(3,2-b) (1,3)benzoxazin-10-one Salicylhydroxamic acid (30 g.) and 36 g. of 4-chlorobutyraldehyde diethyl acetal were allowed to react in acetic acid as described in Example 1. The reaction mixture was transferred to an ice-water mixture, stirred well, and decanted to remove the aqueous layer. The oil was washed again with water and allowed to stand at room temperature whereupon crystallization occurred. Aqueous solution of ammonium hydroxide was added, mixture was warmed and stirred and then allowed to stand overnight at room temperature. The aqueous solution was decanted from the partially crystallized oil and the latter was triturated with ethanol yielding 9.5 g. of solid melting at 137.5°–139.5° C. After recrystallization from methanol, the product (7 g.) melted at 139°–141° C.

EXAMPLE 3

Preparation of 8-methyl-2,3,4,4a-tetrahydro-10H-1,2oxazino (3,2-b)(1,3)benzoxazine-10-one 14.1 g. of 4-chlorobutyryl chloride was dissolved in a mixture of 100 ml. of benzene and 50 ml. of dimethylformamide containing 2 g. of 5 percent palladium on barium sulfate and hydrogenated in a Parr hydrogenation apparatus at room temperature and 50 psig. The mixture was filtered and 12.5 g. of 5-methyl salicylhydroxamic acid was added followed by treatment with hydrogen chloride gas for about one hour. The reaction mixture was then cooled and 400 ml. of cold water was added with stirring. The two layers were separated and the organic layer was washed with water and concentrated to dryness in vacuo. The residue was heated for about 10 min. in boiling ammonium hydroxide (about 100 ml.), cooled, and the solid was removed by filtration. The solid was recrystallized from isopropanol with the aid of Norite giving 8.8 g. of product melting at 133°–135° C.

EXAMPLE 4

Preparation of 8-chloro-2-methyl-2,3,4,4a-tetrahydro-10H-1,2-oxazino(3,2-b)(1,3)benzoxazin-10-one A mixture of 30 g. of γ-valerolactone, 30 ml. of distilled thionyl chloride and 0.5 g. of zinc chloride was heated on a steam bath overnight and then distilled at 15 mm. The distillate was redistilled at 69–70° and 15 mm. giving 34 g. of 4-chlorovaleryl chloride. The acid chloride was reduced catalytically, reacted with 5-chlorosalicylhydroxamic acid and the resulting intermediate was ring-closed according to the method described in Example 3. The product after recrystallization from trichloroethylene weighed 8.5 g. and melted at 210–213° C.

EXAMPLE 5

Preparation of 8-chloro-3-methyl-2,3,4,4a-tetrahydro-10H-1,2-oxazino(3,2-b)(1,3)benzoxazin-10-one 80 g. of the methyl half ester of 3-methylglutaric acid (Linstead, lunt and Weedon, J. Chem. Soc. 1950, 3331) was converted to methyl 4-bromo-3-methylbutyrate as described by Marks and Polgar, J. Chem. Soc. 1955, 3854. The bromoester (51 g.) was reduced with sodium bis (2-methoxyethoxy)aluminum hydride in a mixture of toluene and ether yielding 43 g. of 4-bromo-3-methylbutyraldehyde. The aldehyde and 49 g. of 5-chlorosalicylhydroxamic acid were condensed by the method described in Example 1 and the product was ring-closed with 10 percent aqueous sodium hydroxide to give 8-chloro-3-methyl-2,3,4,4a-tetrahydro-10H-1,2-oxazino(3,2-b) (1,3)benzoxazin-10-one which melted at 121–140° C. after recrystallization from ethanol.

EXAMPLE 6

Preparation of 8-chloro-4-methyl-2,3,4,4a-tetrahydro-10H-1,2-oxazino(3,2-b)(1,3)benzoxazin-10-one 40 g. of 2-methylbutyrolactone was converted to 45 g. of 4-chloro-2-methylbutryl chloride (b.p. 70°–72° C at 15 mm.) by the method detailed in Example 4. The acid chloride (15.5 g.) was reduced to the corresponding aldehyde, condensed with 5-chlorosalicylhydroxamic acid and the resulting intermediate was ring-closed according to the method described in Example 3. The product melted at 144°–146° C. after recrystallization from a mixture of trichloroethylene and hexane.

The analytical data for the exemplary compounds prepared in accordance with Examples 1–6 set out in Table 1 below

TABLE I

| Compound of Example | X | $R_1$ | $R_2$ | $R_3$ | M.P. ° C | Formula | Analysis, Percent Calculated | | | | Found | | | |
|---|---|---|---|---|---|---|---|---|---|---|---|---|---|---|
| | | | | | | | C | H | N | Cl | C | H | N | Cl |
| 1 | 8-Cl | H | H | H | 148–149 | $C_{11}H_{10}ClNO_3$ | 55.14 | 4.20 | 5.83 | | 55.42 | 4.34 | 5.73 | |
| 2 | H | H | H | H | 139–141 | $C_{11}H_{11}NO_3$ | 64.38 | 5.40 | 6.83 | | 64.24 | 5.59 | 6.90 | |
| 3 | 8-CH$_3$ | H | H | H | 133–135 | $C_{12}H_{13}NO_3$ | 65.75 | 5.94 | 6.39 | | 65.75 | 6.03 | 6.27 | |
| 4 | 8-Cl | CH$_3$ | H | H | 210–213 | $C_{12}H_{12}ClNO_3$ | 56.83 | 4.77 | 5.52 | 13.98 | 56.65 | 4.58 | 5.37 | 14.10 |
| 5 | 8-Cl | H | CH$_3$ | H | 121–140 | $C_{12}H_{12}ClNO_3$ | 56.83 | 4.77 | 5.52 | 13.98 | 56.71 | 4.60 | 5.39 | 13.93 |
| 6 | 8-Cl | H | H | CH$_3$ | 144–146 | $C_{12}H_{12}ClNO_3$ | 56.83 | 4.77 | 5.52 | 13.98 | 56.92 | 4.86 | 5.83 | 14.10 |

By using salicylhydroxamic acid having more than one substituent thereon, i.e., dialkyl, dihalo or haloalkyl, it will be readily apparent to one skilled in the art that additional compounds such as the 6,8-dichloro, 6,8-dimethyl and 6-chloro-7-methyl derivatives can be prepared.

The compounds of the present invention are useful as a result of their valuable pharmacological properties, for example, they are valuable anti-inflammatory agents, as evidenced by their ability to inhibit the local edema formation characteristic of inflammatory states when administered systemically to warm-blooded animals.

The procedure described below (Winters et al, *Proc. Soc., Exp. Biol. Med.*, 111, 544, 1962) was used to establish the effectiveness of these compounds in the hind paw edema induced by carrageenin in the rat. This procedure is considered suitable for demonstrating anti-inflammatory activity of drug compounds in laboratory animals.

Male rats of the Sprague-Dawley strain (Charles River Laboratories) weighing 100 ± 20 grams were used for this study. Six animals were used for each drug dose. The drug was suspended in 1 percent aqueous solution of gum acacia, and each rat received 10 ml/kg of the appropriate concentration of drug suspension by oral intubation; controls were given a similar volume of the vehicle. One hour later, edema in the right hind paw was induced by the subplantar injection of 0.05 ml. of 1 percent calcium carrageenin dissolved in 0.15N sodium chloride. The volume of the foot was determined immediately and again 3 hours later. The difference was recorded as edema volume. Foot volume was measured by immersion of the foot in water at the level of the lateral malleolus, and determining the volume of water displaced by the foot. The ED$_{50}$ may be defined as the dose in which edema formation is inhibited by 25 percent or more in 50 percent of the rats when compared to the mean value of the controls.

When tested by the method set forth above, the exemplary compounds of the present invention were found to have an ED$_{50}$ as set forth in Table 11.

TABLE II

| Compound of Example | ED$_{50}$ ± SE |
|---|---|
| 1 | 100 ± 27 |
| 2 | 65 ± 22 |
| 3 | >300 |
| 4 | 270 ± 185 |
| 5 | 160 ± 73 |

TABLE II-continued

| Compound of Example | $ED_{50} \pm SE$ |
| --- | --- |
| 6 | 195 ± 96 |

The pharmaceutical compositions of the present invention are prepared by incorporating the active ingredient with a suitable pharmaceutical carrier. The carrier must be of such nature that the novel compositions may be administered systemically to warm-blooded animals. The term "systemically" as used herein, means a mode of administration whereby the active ingredient, when given to warm blooded animals, is effective in the whole body and not merely at the locus of application. This includes parenteral and other methods of administration.

The active ingredients of the present invention are preferably administered orally in the form of tablets or capsules. Suitable solid pharmaceutical carriers which can be utilized include, for example, starch, lactose, sucrose, glucose, gelatin, and the like. When the composition is in the form of a solid, the active ingredient is generally in the amount of from about 25 to about 95 percent by weight of the total composition.

The active ingredients of the invention can also be dissolved in a liquid pharmaceutical carrier, such as, for example, propylene glycol, polyethylene glycol, water, saline, and mixtures thereof, to form a solution suitable for injection. Such injectable solutions generally contain from about 0.05 gram to about 30 grams of active ingredient per 100 ml. of solution.

What is claimed is:

1. A compound of the formula:

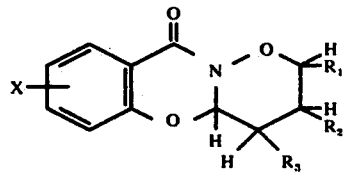

wherein X is hydrogen or lower alkyl, $R_1$ and $R_2$ are hydrogen and $R_3$ is hydrogen or lower alkyl.

2. 2,3,4,4a-tetrahydro-10H-1,2-oxazino(3,2-b)(1,3)benzoxazin-10-one.

* * * * *